United States Patent [19]

Imanaka et al.

[11] 4,283,492
[45] Aug. 11, 1981

[54] PRODUCTION OF ANTIBIOTICS WS-3442 A, B, C, D AND E, AND THEIR ACYL DERIVATIVES

[75] Inventors: Hiroshi Imanaka; Junzi Hosoda, both of Ikeda; Kazuyoshi Jomon, Kawanishi; Heiichi Sakai, Ikeda; Ikuo Ueda, Yao; Daizou Morino, Hatsutoriyutakamachi, all of Japan

[73] Assignee: Fujisawa Pharmaceutical Co., Ltd., Osaka, Japan

[21] Appl. No.: 915,215

[22] Filed: Jun. 13, 1978

Related U.S. Application Data

[62] Division of Ser. No. 371,989, Jun. 21, 1975, abandoned.

[51] Int. Cl.$^2$ .................................................. C12D 9/14
[52] U.S. Cl. ...................................... 435/47; 435/886
[58] Field of Search ............................. 195/36 C, 80 R

[56] References Cited

U.S. PATENT DOCUMENTS

| | | | |
|---|---|---|---|
| 3,739,002 | 6/1973 | Hayes et al. | 260/243 C |
| 3,769,169 | 10/1973 | Birnbaum et al. | 195/80 R |
| 3,769,281 | 10/1973 | Chauvette | 260/243 C |
| 3,770,590 | 11/1973 | Inamine et al. | 195/80 R |
| 3,819,619 | 6/1974 | Horii et al. | 260/243 C |
| 3,819,621 | 6/1974 | Morimoto et al. | 260/243 C |

FOREIGN PATENT DOCUMENTS 957569  5/1964  United Kingdom .................... 540/30

*Primary Examiner*—Lionel M. Shapiro
*Attorney, Agent, or Firm*—Dayton R. Stemple, Jr.

[57] ABSTRACT

Production of antibiotic WS-3442 A, B, C, D and E, and their acyl derivatives thereof, the production of antibiotic WS-3442 A, B, C, D and E being a new method by culturing a new species of Streptomyces and their acyl derivatives of said antibiotics being prepared by acylating said antibiotics with an acylating agent. The acyl derivative of antibiotic WS-3442 A, B, C, D and E has antimicrobiological activity and is also useful for intermediate for preparing Cephalosporin derivatives having antimicrobiological activity.

9 Claims, 5 Drawing Figures

FIG. 1

ULTRAVIOLET ABSORPTION SPECTRUM
OF WS-3442 A
(IN PHOSPHATE BUFFER)

FIG. 2

ULTRAVIOLET ABSORPTION SPECTRUM
OF WS-3442 B
(IN WATER)

FIG. 3

ULTRAVIOLET ABSORPTION SPECTRUM
OF WS-3442 C
(IN WATER)

FIG. 4

ULTRAVIOLET ABSORPTION SPECTRUM
OF WS-3442 D
(IN PHOSPHATE BUFFER)

FIG. 5

ULTRAVIOLET ABSORPTION SPECTRUM
OF WS-3442 E
(IN WATER)

PRODUCTION OF ANTIBIOTICS WS-3442 A, B, C, D AND E, AND THEIR ACYL DERIVATIVES

This is a division, of application Ser. No. 371,989, filed June 21, 1973, now abandoned.

This invention relates to the production of antibiotic WS-3442 A,B,C,D and E, and furthermore to their acyl derivatives and the production of said acyl derivatives.

More particularly, it relates to a new method for production of antibiotic WS-3442 A,B,C,D and E by culturing a new species of Streptomyces named by us *Streptomyces wadayamensis* in a nutrient medium, and to the acyl derivatives of these antibiotic WS-3442 A,B,C,D and E and a method for the production thereof.

Accordingly, it is one object of this invention to provide a new method for the production of antibiotic WS-3442 A,B,C,D and E by fermentation of *Streptomyces wadayamensis* in a nutrient medium.

Another object of this invention is to provide the acyl derivatives of WS-3442 A,B,C,D and E, which are also active against microorganisms.

A further object of this invention is to provide a method for the preparation of the acyl derivatives of antibiotic WS-3442 A,B,C,D and E by treating the broth containing WS-3442 A,B,C,D and E with an acylating agent.

WS-3442 A,B,C,D and E are each a known compound having, the following chemical structure described in the literatures as listed below, respectively.

| WS-3442 | R | R' |
|---|---|---|
| A | H | H |
| B | H | OCONH$_2$ |
| C | OCH$_3$ | OCONH$_2$ |
| D | OCH$_3$ | H |
| E | H | OH |

Literature:

WS-3442 A: British Patent No.957,543

WS-3442 B: Journal of the American Chemical Society, 93, No.9, P.2308–2310.

WS-3442 C: Japanese Patent Early Publication No.3286/1971. Journal of the American Chemical Society, 93, No.9, P.2308–2310.

WS-3442 D: Japanese Patent Early Publication No. 3286/1971.

WS-3442 E: Biochemical Journal, 81, P.591–596 (1961).

Further, a method for the production of WS-3442 B by culturing *Streptomyces clavuligerus* is described in "Program and Abstracts," P.13 of ELEVENTH INTERSCIENCE CONFERENCE ON ANTIMICROBIAL AGENTS AND CHEMOTHERAPY (19–22 October, 1971).

A method for the production of antibiotic WS-3442 C by culturing *Streptomyces lactamdurans* is also described in the specification of Japanese Patent Early Publication No.3286/1971.

However, a method for the production of antibiotic WS-3442 A, D and E by fermentation have not been found in any publication.

A method for production of antibiotic WS-3442 A,B,C,D and E is conducted by culturing a new species of Streptomyces named by us *Streptomyces wadayamensis*.

THE MICROORGANISM

The microorganism useful for a method for production of antibiotic WS-3442 A,B,C,D and E is a newly discovered species of Streptomyces isolated from a soil sample collected in Wadayamacho, Hyogo Prefecture, Japan.

A culture of the living organism has been deposited with, and added to a permanent stock culture collection of, the American Type Culture Collection, under the number ATCC 21948 and is hereinafter designated as *Streptomyces wadayamensis*.

It is to be understood that, for the production of these antibiotics, this invention is not limited to the use of the particular organism described herein, which is given for illustrative purpose. This invention also may include the use of mutants produced from the described organism by conventional means, such as X-rays, ultra-violet radiation, nitrogen mustards, etc.

*Streptomyces wadayamensis* ATCC 21948 shows the following morphological, cultural and physiological characteristics.

1. Morphological characteristics:

The morphology of the culture was microscopically observed with mycelium grown on inorganic salts-starch agar at 30° C. for 10–15 days.

The aerial hyphae of this culture is branched closely and the top of the aerial hyphae is looped or spiral and forms a chain of conidia.

The conidium is spherical or elliptical and the surface of the conidium is spiny.

2. Cultural characteristics:

The strain has the following cultural characteristics when grown on media as indicated below at 30° C. for 10–15 days.

| Medium | Growth | Aerical mycelium | Soluble pigment | Remarks |
|---|---|---|---|---|
| CZAPEK's agar | flat, spreading, faint creamy yellow | poor, powdery, white | none | |
| Glucose-asparagine agar | flat, spreading, ivory | poor, powdery, white | none | |
| Glycerol asparagine agar | flat, spreading, faint creamy | poor, powdery, white | none | |
| Inorganic salts-starch agar | wrinkled, somewhat raised, grayish yellow | powdery, gray and white | none | hydrolysis of starch: moderate |

-continued

| Medium | Growth | Aerical mycelium | Soluble pigment | Remarks |
|---|---|---|---|---|
| | | | | to strong |
| Tyrosine agar | wrinkled, dark brown | powdery, faint grayish brown | none | |
| Nutrient agar | yeast-like, grayish creamy | none | brown | |
| yeast malt agar | faint brown | cottony, existed water drops, faint gray, white | none | |
| Oatmeal agar | faint yellow | powdery, gary | none | |
| Peptone-yeast-iron agar | flat, dark gray | none | dark brown | |
| BEBNETT's agar | white | cottony, graish white | none | same growth at 37° C. |
| Milk | ring, dark gray | powdery, partly white | graish brown | coagulation: weak peptonization: weak |
| Gelatin stab (at room temperature for 20 days) | wrinkled, black | powdery, gray | black (restricted diffusion) | liquefaction: weak |

3. Physiological characteristics:
 (1) Optimum temperature for growth:
 30°–37° C.
 (2) Optimum PH for growth:
 6–8
 (3) Production of tyrosinase:
 Not recognized
 (4) Production of melanin-like pigment:
 Recognized
 (5) Hydrolysis of starch:
 Hydrolyzed
 (6) Liquefaction of gelatin:
 Not liquidized
 (7) Coagulation and peptonization of skim milk:
 Not recognized
4. Carbon source utilization patterns by Pridham-Gottlieb method:

| Source of carbon | Growth |
|---|---|
| L-Arabinose | ± |
| D-Xylose | ± |
| D-Glucose | + |
| D-Fructose | + |
| Rhamnose | − |
| Sucrose | + + |
| Raffinose | − |
| D-Mannitol | + + |
| Inositol | + |

+ + = Good utilization.
+ = Utilization.
± = Probable utilization.
− = No utilization.

ANTIBIOTIC WS-3442 A,B,C,D and E

The antibiotic WS-3442 A,B,C,D and E are produced when a strain belonging to Streptomyces wadayamensis is grown in a nutrient medium containing assimilable sources of carbon and of nitrogen, and an inorganic salt under controlled submerged aerobic conditions. The nutrient medium may be any one of a number of media which can be utilized by a strain belonging to Streptomyces wadayamensis.

The prefered sources of carbon in the nutrient medium are carbohydrates such as glucose, fructose, sucrose, mannitol glycerin and starch. Other sources which may be included are arabinose, xylose, inositol, sugar, dextrin, molasses and the like.

The prefered sources of nitrogen are meat extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea and the like.

The carbon and nitrogen sources, though advantageously employed in combination, need not be used in their pure form because less pure materials, which contain traces of growth factors, and considerable quantities of mineral nutrients, are also suitable for use. When desired, there may be added to the medium mineral salts such as calcium carbonate, sodium or potassium phosphate, sodium or potassium chloride, magnesium salt, copper salt and the like. If necessary, especially when the culture medium is foamed remarkably, a defoaming agent, such as liquid paraffin, fatty oil, plant oil, mineral oil and silicones, may be added.

As is preferred for the production of other antibiotics in massive amounts, submerged aerobic cultural conditions are preferred for the production of WS-3442 A,B,C,D and E in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the antibiotics. Accordingly, it is desirable first to produce a vegetative inoculum of the organism by inoculating a relatively small quantity of culture medium with spores or mycelia of the organism and culture them and to transfer the cultured vegetative inoculum aseptically to large tanks. The medium in which the vegetative inoculum is produced can be the substantially same as or different from medium utilized for the production of the WS-3442 A,B,C,D and E.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably 30° C., for a period of 30 hours to 100 hours.

The antibiotics WS-3442 A,B,C,D and E according to this invention, can be recovered from the culture medium by conventional means which are commonly used for the recovery of other antibiotics.

In general, most of these antibiotics produced are found in the cultured broth, and accordingly these antibiotics can be separated from the filtrate, which is obtained by filtrating or centrifuging the broth, by a conventional method, e.g. an extractive or adsorptive techniques.

Extraction is conducted by treating the filtrate with an organic solvent in which these antibiotics can be soluble, for example, pyridine, alcohols such as methanol, ethanol, butanol, etc., ketones such as acetone etc., or aqueous alcohol such as aqueous methanol, ethanol and butanol or which an alkaline aqueous solution such as aqueous pyridine, aqueous ammonium, aqueous sodium hydroxide and the like. Other solvents of similar character may also be used. Combination of these solvents are advantageously employed.

Alternatively, these antibiotics can be separated from the culture broth by making these antibiotics in the filtered broth adsorbed on adsorbing agents such as activated carbon, activated alumina, silica gel, magnesium aluminum silicate, ion exchange resin and cellulose powder, and by eluting these antibiotics adsorbed from the adsorbents by employing a polar, organic solvent in which these antibiotics are soluble.

These antibiotics may be isolated from the extract or the eluate thus obtained by adding a suitable solvent, in which these antibiotics are insoluble, to the solution or alternatively by adjusted pH of the solution, so that these antibiotics may be precipitated in the solution. In this isolation process, it is to be understood that, when desired, the extract or the eluate may be concentrated to a relatively small volume by evaporating the solvent. Thus isolated antibiotics are purified by a conventional method, e.g. recrystallization or chromatography.

WS-3442 A,B,C,D and E which are isolated in this manner are each confirmed to be a known compound having the following chemical structure by way of the results of the following experiments, interpretation of the physical and chemical properties as mentioned below, and also other researchs.

WS-3442 A 7-(5-Amino-5-carboxyvaleramido)-3-methyl-3-cephem-4-carboxylic acid.

Figure 1:
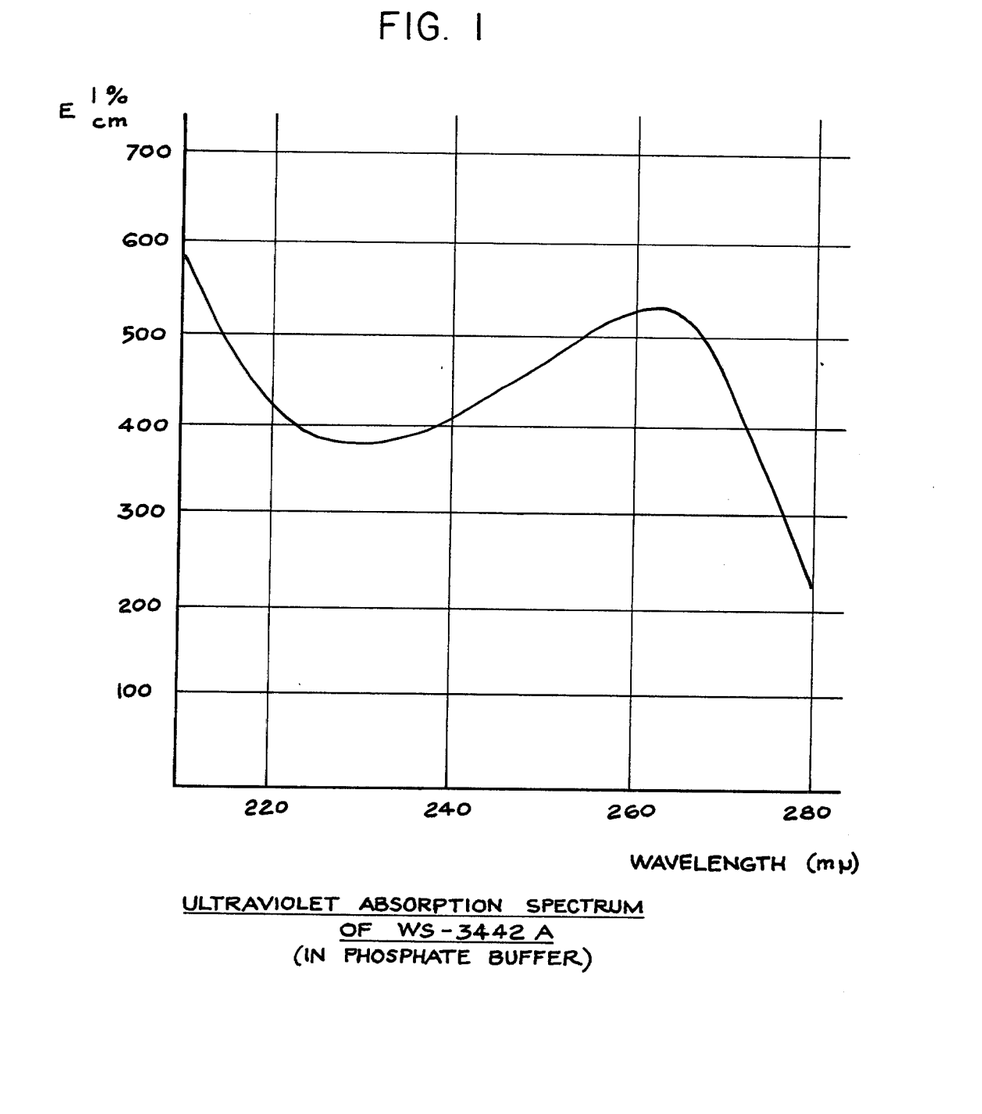

WS-3442 A is white powder, and the ultra-violet absorption spectrum (solvent: phosphate buffer solution (PH 6.4)) as shown in FIG. 1 of the accompanying drawing shows the maximum at 262 m$\mu$ (E % 143). The infra-red absorption spectrum (suspended in Nujol mull) gives the peak at 1760 cm$^{-1}$ being due to the carbonyl of the 4-membered lactam. The nuclear magnetic resonance spectrum gives the following signals ($\delta$ ppm; in deuterium; TMS internal standard).

1.85 (4H, multiplet)
2.01 (3H, singlet)
2.45 (2H, multiplet)
3.23~3.65 (2H, doublet, J=18 HZ)
3.80 (1H, multiplet)
5.1 (1H, doublet, J=4.5 HZ)
5.58 (1H, doublet, J=4.5 HZ)
8.32 (1H, singlet)

The Rf value in thin layer chromatography is determined using ninhydrin as a colouring agent and the mixture of n-butanol, acetic acid and water (4:1:2) as a solvent system, and the Rf value is 0.19.

Experiment 1

A powder (40 mg) of WS-3442-A obtained in the following example 1 was dissolved in a phosphate buffer solution (2 ml) at pH 7.0, and phenyl isocyanate (0.1 ml) was added dropwise thereto under stirring. Then, the mixture was stirred for an hour, and diphenyl urea was separated off, after confirmation of Ninhidrin test being negative. The aqueous layer was adjusted to pH 1.0 to 1.5 with 0.1 N hydrochloric acid and extracted with ethyl acetate. The ethyl acetate layer was washed with an aqueous solution saturated with sodium chloride and dried over magnesium sulfate, after which the solvent was distilled off under reduced pressure. The resultant residue was dried to give a white powder (30 mg).

| Nuclear Magnetic Resonance: | |
|---|---|
| Solvent: Deuterium + sodium bicarbonate | |
| Internal Standard: TMS | |
| $\delta$ value (ppm) | |
| 1.80 | (4H, quartet) |
| 1.90 | (3H, singlet) |
| 2.40 | (2H, multiplet) |
| 3.02 to 3.52 | (2H, quartet, J = 18HZ) |
| 4.17 | (1H, multiplet) |
| 5.06 | (1H, doublet, J = 4.5HZ) |
| 5.55 | (1H, doublet, J = 4.5HZ) |
| 7.35 | (5H, multiplet) |

Thin Layer Chromatography:
Solvent system: Acetic acid: Ethyl acetate (1:2)
Rf Value: 0.58
Melting Point of the di-dicyclohexylamine salt:
mp 201 to 205° C.
Analysis calculated for $C_{45}H_{70}N_6O_7S \cdot 2H_2O$
(the di-dicyclohexylamine salt)
C 61.80, H 8.51, N 9.60
Found C 62.09, H 8.35, N 9.67

EXPERIMENT 2

Sodium 7-(5-amino-5-carboxyvaleramido)-3-methyl-3-cephem-4-carboxylate (I) (2.0 g), which is a known compound by publications, e.g. British Pat. No. 957,543, was dissolved in a phosphate buffer solution (75 ml) at pH 7.0 and phenyl isocyanate (2.0 ml) was added dropwise thereto under stirring at room temperature. After confirmation of the Ninhydrin test being negative, precipitating diphenylurea was filtered off. The aqueous layer was adjusted to pH 1.0 to 1.5 with N hydrochloric acid and extracted with ethyl acetate. The ethyl acetate layer was washed with an aqueous solution saturated with sodium chloride, and dried over magnesium sulfate after which the solvent was distilled off under reduced pressure to give a faint yellow powder (500 mg). This powder was recrystallized from 60% methanol to give white powder of 7-[5-(3phenylureido)-

5-carboxyvaleramido]-3-methyl-3-cephem-4-carboxylic acid having mp 150°-162° C.

Analysis calculated for $C_{21}H_{24}N_4SO_7.\frac{1}{2}H_2O$ C, 52.0, H 5.16, N 11.55, $H_2O$ 1.85, Found: C 52.18, H 5.19, N 11.49, $H_2O$ 1.99

| Nuclear Magnetic Resonance: | |
|---|---|
| Solvent: deuterium + sodium bicarbonate | |
| Internal Standard: TMS | |
| δ Value (ppm) | |
| 1.80 | (4H, multiplet) |
| 1.90 | (3H, singlet) |
| 2.40 | (2H, multiplet) |
| 3.02 to 2.52 | (2H, quartet) |
| 4.17 | (1H, multiplet) |
| 5.06 | (1H, doublet, J = 4.5HZ) |
| 5.55 | (1H, doublet, J = 4.5HZ) |
| 7.35 | (5H, multiplet) |

Thin Layer Chromatography:
Solvent system: Acetic acid: Ethyl acetate (1:2)
Rf Value: 0.58
Melting Point of the di-dicyclohexylamine: mp 203 to 205° C.

WS-3442 B 7-(5-Amino-5-carboxyvaleramido)-3-(carbamoyloxy methyl)-3-cephem-4-carboxylic acid.

Figure 2:
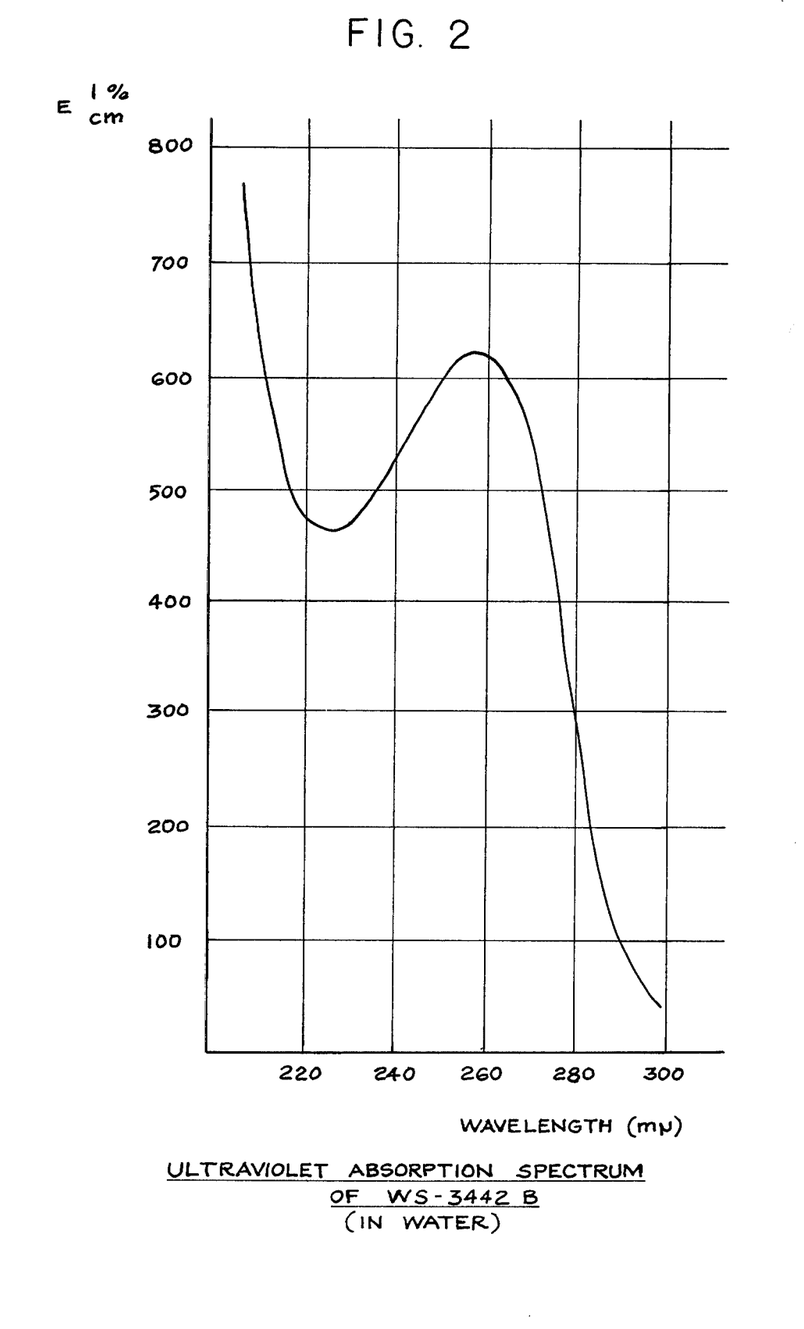

The ultra-violet absorption spectrum of WS-3442 B (solvent:water) as shown in FIG. 2 of the accompanying drawing shows maximum at 261 mμ. The infra-red absorption spectrum (suspended in Nujol mull) gives the peak at 1770 cm$^{-1}$ due to the carbonyl of 4-membered lactam. The nuclear magnetic resonance spectrum gives the following signals (δ ppm; in deuterium; TMS internal standard).

| 1.84 | (4H, multiplet) |
|---|---|
| 2.40 | (2H, multiplet) |
| 3.30~3.80 | (2H, quartet, J = 18HZ) |
| 3.80 | (1H, multiplet) |
| 4.78 | (2H, quartet, J = 13.0HZ) |
| 5.12 | (1H, doublet, J = 4.5HZ) |
| 5.60 | (1H, doublet, J = 4.5HZ) |

WS-3442 C 7-(5-Amino-5-carboxyvaleramido)-3-(carbamoyloxymethyl)-7-methoxy-3-cephem-4-carboxylic acid.

Figure 3:
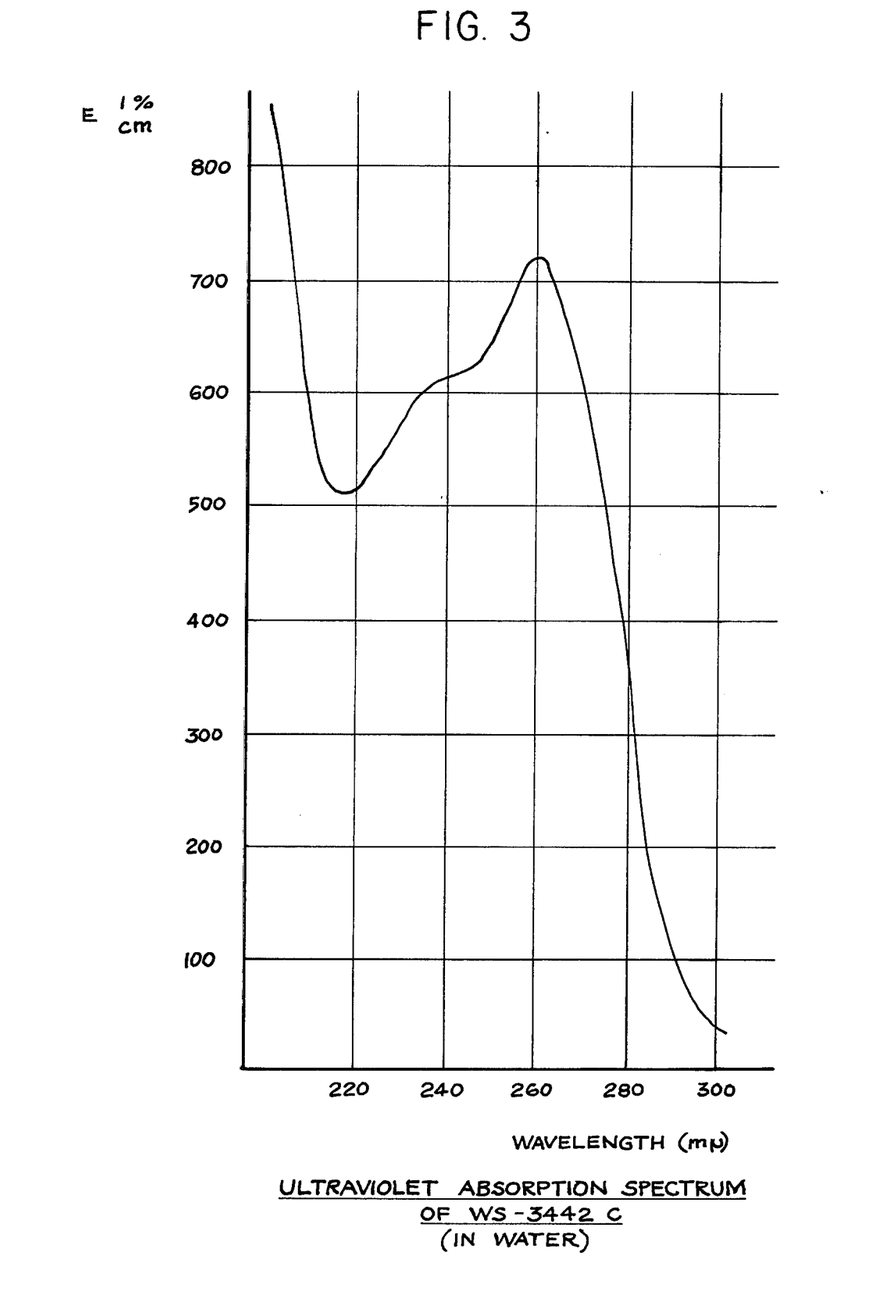

The ultra-violet absorption spectrum of WS-3442 C (solvent:water) as shown in FIG. 3 of the accompanying drawing shows the maxima at 242 mμ and 264 mμ. The infra-red absorption spectrum (suspended in Nujol mull) gives the peak at 1770 cm$^{-1}$ due to the carbonyl of 4-membered lactam. The nuclear magnetic resonance spectrum gives the following signals (δ ppm; in deuterium; TMS internal standard).

| 1.90 | (4H, multiplet) |
|---|---|
| 2.50 | (2H, multiplet) |
| 3.25~3.70 | (2H, quartet, J = 18HZ) |
| 3.58 | (3H, singlet) |
| 3.75 | (1H, multiplet) |
| 4.75 | (2H, quartet, J = 13.0 HZ) |
| 5.20 | (1H, singlet) |

WS-3442 D 7-(5-Amino-5-carboxyvaleramido)-3-methyl-7-methoxy-3-cephem-4-carboxylic acid.

Figure 4:
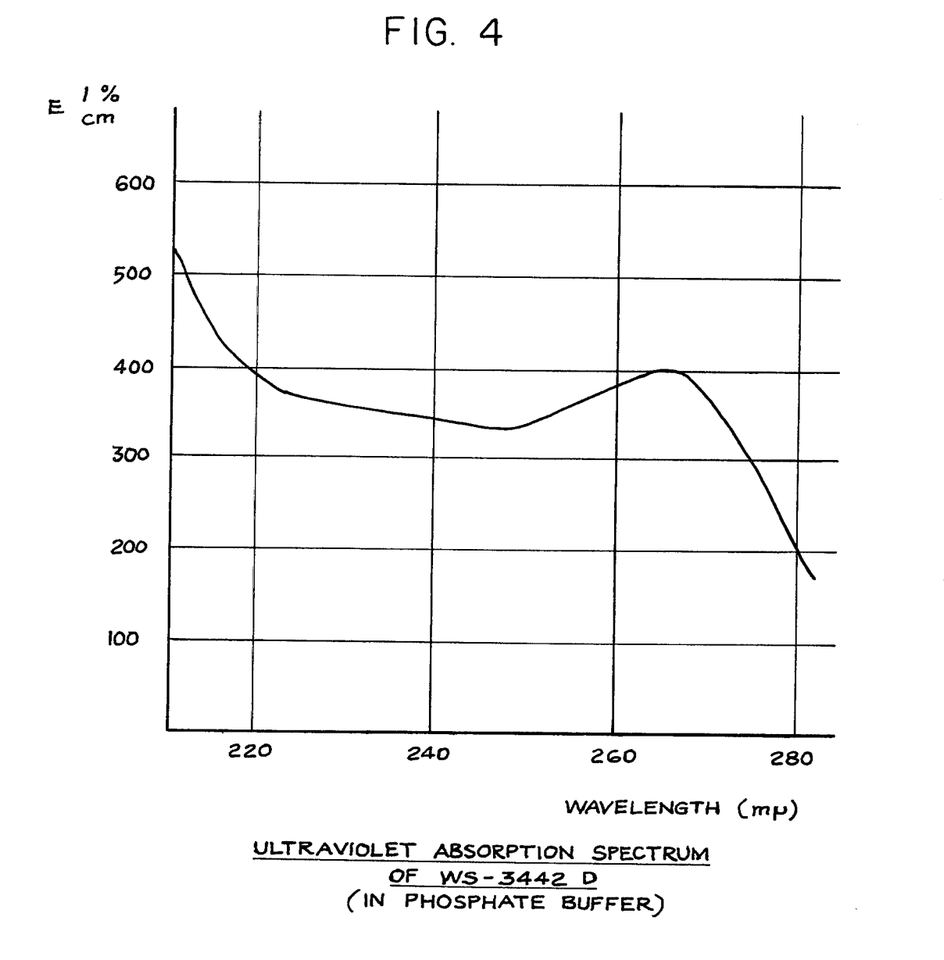

WS-3442 D is pale yellow powder, and the ultra-violet absorption spectrum (solvent:phosphate buffer solution (pH 6.4)) as shown in FIG. 4 of the accompanying drawing shows the maximum at 263 mμ (E%=106). The infra-red absorption spectrum (suspended in Nujol mull) gives the peak at 1760 cm$^{-1}$ due to the carbonyl of the 4-membered lactam. The nuclear magnetic resonance spectrum gives the following signals (δ ppm; in deuterium; TMS internal standard).

| 1.85 | (4H, multiplet) |
|---|---|
| 2.04 | (3H, singlet) |
| 2.45 | (2H, multiplet) |
| 3.17-3.68 | (2H, doublet J = 18HZ) |
| 3.56 | (3H, singlet) |
| 3.85 | (1H, multiplet) |
| 5.15 | (1H, singlet) |

The Rf value in thin layer chromatography was determined using ninhydrin as a colouring agent and the mixture of acetonitrile and water (5:2) as a solvent system, and the Rf value is 0.55.

EXPERIMENT 1

To a mixture of 7-(5-amino-5-carboxyvalerlamido)-3-carbamoyloxymethyl-7-methoxy-3-cephem-4-carboxylic acid (12.0 g), which is known compound by publications, e.g., Journal of the Americal Chemical Society, Vol. 93, No. 9, 2308, water (120 ml) and sodium bicarbonate (5.0 g), a solution of t-butoxycarbonyl azide (5.5 g) in dioxane (60 ml) was added thereto under stirring. The reaction mixture was stirred for 6 hours, after which the dioxane was distilled off. To the residue was added ice-water, and the mixture was saturated with sodium chloride and extracted with ethyl acetate. The aqueous layer was adjusted to pH 2.0 under ice-cooling and extracted with ethyl acetate. The extract was washed with water and dried over magnesium sulfate, after which the solvent was distilled off under reduced pressure to give faint yellow powder (2.2 g) of 7-(5-t-butoxycarbonylamino-5-carboxyvaleramido)-3-carbamoyloxymethyl-7-methoxy-3-cephem-4-carboxylic acid.

| Nuclear Magnetic Resonance: | |
|---|---|
| Solvent: deuterium + sodium bicarbonate | |
| Internal Standard: TMS | |
| δ value (ppm): | |
| 1.43 | (9H, singlet) |
| 1.75 | (4H, multiplet) |

| | |
|---|---|
| 2.40 | (2H, multiplet) |
| 3.25 to 3.72 | (2H, doublet, J = 18HZ) |
| 3.53 | (3H, singlet) |
| 3.85 | (1H, multiplet) |
| 5.16 | (1H, singlet) |

Thin Layer Chromatography:

Solvent system: Acetic acid: Ethyl acetate (1:2)
Rf Value: 0.49

EXPERIMENT 2

A mixture of paradium hydroxide and barium sulfate was added to 7-(5-t-butoxycarbonylamino-5-carboxyvaleramido)-3-carbamoyloxymethyl-7-methoxy-3-cephem-4-carboxylic acid (2.1 g) obtained in the above, water (20 ml) and sodium bicarbonate (1.02 g) in a 250 ml-vessel for moderate catalytic reduction. The resultant mixture was subjected to moderate reduction for 3 hours in the present of a mixture (6.8 g) of paradium hydroxide and barium sulfate, after which ice-water and ethyl acetate were added thereto in order. The resultant mixture was adjusted to pH 2.0 with 0.5 N hydrochloric acid, filtered and washed with ethyl acetate. The aqueous layer was saturated with sodium chloride and extracted with ethyl acetate. The ethyl acetate layer was washed with water and dried over magnesium sulfate, and the solvent was distilled off under reduced pressure to give faint yellow powder (1.1 g) of 7-(5-t-butoxycarbonylamino-5-carboxyvaleramido)-3-methyl-7-methoxy-3-cephem-4-carboxylic acid.

Nuclear Magnetic Resonance:
Solvent: deuterium + sodium bicarbonate
Internal Standard: TMS

| δ value (ppm) | |
|---|---|
| 1.43 | (9H, singlet) |
| 1.75 | (4H, multiplet) |
| 1.92 | (3H, singlet) |
| 2.40 | (2H, multiplet) |
| 3.10 to 3.60 | (2H, doublet, J = 18HZ) |
| 3.51 | (3H, singlet) |
| 3.90 | (1H, multiplet) |
| 5.11 | (1H, singlet) |

Thin Layer Chromatography:

Solvent system: Acetic acid: Ethyl acetate (1:2)
Rf Value: 0.67

EXPERIMENT 3

A mixture of 7-(5-t-butoxycarbonylamino-5-carboxyvaleramido)-3-methyl-7-methoxy-3-cephem-4-carboxylic acid (1.0 g) and 98% formic acid (10 ml) was stirred for an hour, after which the formic acid was distilled off.

To the resultant residue was added ethyl acetate (10 ml) and the ethyl acetate was distilled off under reduced pressure. The residue was dissolved in water (10 ml), and the 25% Amberlite LA-1:methyl:isobutyl:ketone solution (trademark) (10 ml) was added thereto. The resultant mixture was stirred for an hour, from which the aqueous layer was separated out. The organic solvent layer was washed with water (5 ml), and the washings and the aqueous layer obtained above were taked together and washed with ethyl acetate. The aqueous layer was treated with active carbon and the solvent was distilled off under reduced pressure. The residue was lyophillized to give faint yellow powder (650 mg) of 7-(5-amino-5-carboxyvaleramido)-3-methyl-7-methoxy-3-cephem-4-carboxylic acid.

Nuclear Magnetic Resonance:
Solvent: deterium + sodium bicarbonate
Internal Standard: TMS

| δ value (ppm) | |
|---|---|
| 1.85 | (4H, multiplet) |
| 2.40 | (3H, singlet) |
| 2.45 | (2H, multiplet) |
| 3.17 to 3.68 | (2H, doublet, J = 18HZ) |
| 3.56 | (3H, singlet) |
| 3.85 | (1H, multiplet) |
| 5.15 | (1H, singlet |

Thin Layer Chromatography:

Solvent system: Acetonitrile: water (5:2)
Rf Value: 0.55
Ultra-Violet Absorption Spectrum:
λmax 263 mμ (E % 106) in phosphate buffer solution at pH 6.4
Infra-Red Absorption Spectrum (Nujol):
1760 cm$^{-1}$ (lactam)

WS-3442 E 7-(5-Amino-5-carboxyvaleramido)-3-hydroxymethyl-3-cephem-4-carboxylic acid.

Figure 5:
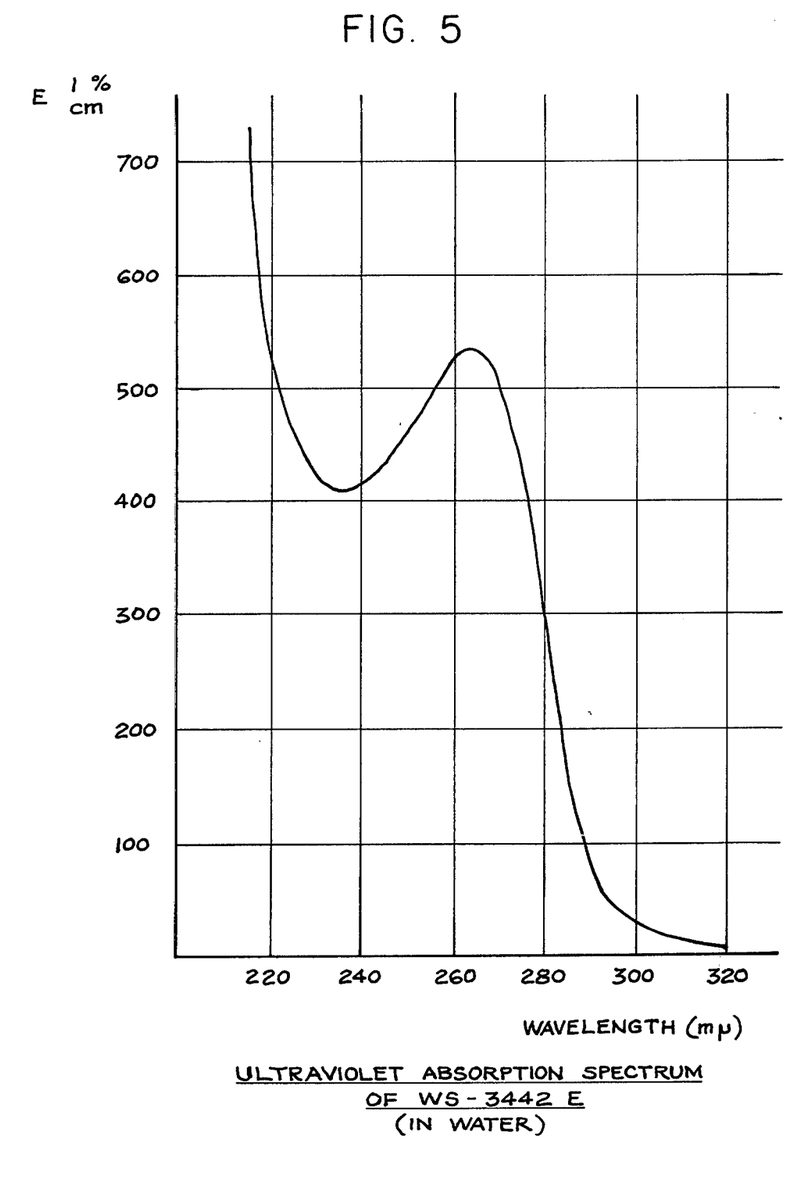

WS-3442 E is pale yellow powder, and the ultra-violet absorption spectrum (solvent:water) as shown in FIG. 5 of the accompanying drawing shows the maximum at 260 mμ (E%=141). The infra-red absorption spectrum (suspended in Nujol mull) gives peak at 1740 cm$^{-1}$ due to the carbonyl of the 4-membered lactam.

The Nuclear magnetic resonance spectrum gives the following signals (δ ppm; in deuterium; TMS internal standard).

| | |
|---|---|
| 1.83 | (4H, multiplet) |
| 2.45 | (2H, multiplet) |
| 3.55 | (2H, doublet, J = 18HZ) |
| 4.27 | (2H, singlet) |
| 5.15 | (1H, doublet, J = 4.5HZ) |
| 5.62 | (1H, doublet, J = 4.5HZ) |

The Rf Value in thin layer chromatography is determined using ninhydrin as a colouring agent and the mixture of n-butanol, acetic acid and water (4:1:2) as a solvent system, and the Rf Value is 0.27~0.32.

EXPERIMENT

To a solution of sodium salt (2.35 g) cepharosporin C in water (23.5 ml) was added acetylesterase (8.5 ml) under stirring at room temperature. The mixture was adjusted to pH 6.6 with 0.2 N sodium hydroxide and allowed to react for 90 minutes, while being kept at pH 6.6. After completion of the reaction, the reaction mixture was lyophillized to give yellowish crystalline powder (2.1 g) of sodium 7-(5-amino-5-carboxyvaleramido)-3-hydroxymethyl-3-cephem-4-carboxylate.

Nuclear Magnetic Resonance:
Solvent: deuterium
Internal Standard: TMS

| δ value (ppm) | |
|---|---|
| 1.83 | (4H, multiplet) |
| 2.45 | (2H, multiplet) |
| 3.55 | (2H, a.b. quartet, J = 18HZ) |
| 4.27 | (2H, singlet) |
| 5.15 | (1H, doublet, J = 4.5 HZ) |
| 5.62 | (1H, doublet, J = 4.5 HZ) |

Thin Layer Chromatography:
Solvent system: n-Butanol: Acetic acid: water (4:1:2)
Rf Value: 0.24 to 0.25
Ultra-Violet Absorption Spectrum:
λ max 262 mμ (E% 142) in citrate buffer solution at pH 6.4
Infra-Red absorption Spectrum (Nujol):
1740 cm$^{-1}$ (lactam)

These antibiotic WS-3442 A,B,C,D and E, produced by the method of this invention, have activities against Bacillus subtilis, Staphylococcus aureus, Escherichia coli, Proteus Vulgaris, etc.

ACYL DERIVATIVES OF ANTIBIOTIC WS-3442 A,B,C,D and E

A method for the production of acyl derivatives of WS-3442 A,B,C,D and E is carried out by reacting a fermentation broth containing WS-3442 A,B,C,D and E with an acylating agent. The process is illustrated in the following scheme:

(Wherein R is a hydrogen or methoxy, R' is hydrogen, hydroxy or carbamoyloxy and A is an acyl group)

As acylating agents to be used in the above reaction, there can be employed all of the acylating agents which are conventionally used. That is, these may be exemplified by an aliphatic, aromatic and heterocyclic carboxylic acid, and the corresponding sulfonic acid, carbonic ester, carbamic acid and thio acid, and the reactive derivatives of the above acids.

As the reactive derivatives, there may be exemplified an acid anhydride, an activated amide, an activated ester, an isocyanate and an isothiocyanate.

As suitable examples of these reactive derivatives are an acid azide, an mixed acid anhydride with an acid such as dialkylphosphoric acid, phenylphosphoric acid, diphenylphosphoric acid, dibenzylphosphoric acid, halogenated phosphoric acid, dialkylphosphorus acid, sulfurous acid, thiosulfuric acid, hydrohalogenic acid (e.g. hydrochloric acid) sulfuric acid, alkylcarbonic acid, aliphatic carboxylic acid (e.g. pivalic acid, pentanoic acid, isopentanoic acid, 2-ethylbutyric acid or trichloroacetic acid), aromatic carboxylic acid (e.g. benzoic acid), or symmetrical acid anhydride, an acid amide with imidazole, 4-substituted imidazole, dimethylpyrazole, triazole or tetrazole, an ester (e.g. cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone, N-hydroxysuccinimide or N-hydroxyphthalimide).

The suitable derivative can be optionally selected from them according to the kind of the acid to be used. In the acylating reaction, when free acid is used, a condensing agent may be preferably added. The suitable examples of the condensing agent may be N,N'-dicyclohexylcarbodiimide, N-cyclohexyl-N'-morpholinoethylcarbodiimide, N-cyclohexyl-N'-(4-diethylaminocyclohexyl) carbodiimide, N,N'-diethylcarbodiimide, N,N'-diisopropylcarbodiimide, N-ethyl-N'-(3-dimethylaminopropyl) carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)-isoxazolium hydroxide intermolecular salt, (chloromethylene)-dimethylammonium chloride, and the like.

The suitable example of an acyl group to be introduced to the amino group of the formula (II) in the acylating reaction may be the radical dehydroxylated from each of an aliphatic, aromatic and heterocyclic carboxylic acid, and the corresponding sulfonic acid, carbonic ester, carbamic acid, and thio acids.

The suitable examples of the acyl group as mentioned above are, more particularly, an alkanoyl group (e.g., acetyl, propionyl, acryloyl, butyryl, isobutyryl, valeryl, isovaleryl, caproyl, heptanoyl, octanoyl, etc.), cycloalkanecarbonyl group (e.g., cyclopentanecarbonyl, cyclohexancarbonyl, etc.) having 2 to 20 carbon atoms, alkenoyl group (e.g., acryloyl, metaacryloyl, crotonoyl, oleoyl, linoleoyl, linolenoyl, etc.) having 2 to 20 carbon atoms, aryloyl group (e.g., benzoyl, toluoyl, naphthoyl, etc.), alkoxycarbonyl group (e.g., methoxycarbonyl, ethoxycarbonyl, propoxycarbonyl, isopropoxycarbonyl, butoxycarbonyl, etc.) having 2 to 20 carbon atoms, aryloxycarbonyl group (e.g., phenyloxycarbonyl, tolyloxycarbonyl, naphthyloxycarbonyl, etc.), aralkyloxycarbonyl group (e.g., benzloxycarbonyl, phenethyloxycarbonyl, etc.), carbon atoms heterocycliccarbonyl group (e.g., nicotinoyl, piperazine-1-carbonyl, morpholine-4-carbonyl, pyrrol-2-carbonyl, furan-2-carbonyl, etc.), alkylcarbonyl group (e.g., succinyl, malonyl, maleoyl, phthaloyl, benzensulfonyl, carbamoyl, methylcarbamoyl, dimethylcarbamoyl, ethylcarbamoyl, propylcarbamoyl, isopropylcarbamoyl, buthylcarbamoyl, etc.), arylcarbamoyl group (e.g., phenylcarbamoyl, tolylcarbamoyl, naphthylcarbamoyl, etc.), and alkylarylcarbamoyl group (e.g., methylphenylcarbamoyl, ethyltolylcarbamoyl, etc.), and the corresponding thiocarbamoyl groups.

In the aforementioned alkanoyl group, cycloalkanecarbonyl group, alkenoyl group, aryloyl group, alkoxycarbonyl group, aryloxycarbonyl group, aralkyloxycarbonyl group, heterocycliccarbonyl group, alkylcarbamoyl group, arylcarbamoyl group and alkylarylcarbamoyl group may be substituted by one or more possible substituents(s) such as hologen (fluorine, chlorine, bromine, iodine), alkoxy group (e.g., methoxy, ethoxy, propoxy, etc.), alkylthio group (e.g., methylthio, ethylthio, propylthio, buthylthio, etc.), aryloxy group (e.g., phenyloxy, tolyloxy, naphthyloxy, etc.), aryl group (e.g., phenyl, tolyl, naphthyl, etc.), alkoxycarbonyl group (e.g., methoxycarbonyl, ethoxycarbonyl, propoxycarbonyl, butoxycarbonyl, etc.), acyloxy group (e.g. acetyloxy, propionyloxy, butyryloxy, benzoyloxy, etc.), acylthio group (acethylthio, propionylthio, butyrylthio, benzoylthio, etc.), acylamino group (e.g., formamido, acetamido, butylamido, propionamido, benzamido, t-butoxycarbonylamido, allyloxycarbonylamino, cyclohexyloxycarbonylamino, phenoxycarbonylamino, phenylthiocarbonylamino, benzyloxycarbonylamino, toluenesulfonylamino, etc.), and heterocyclic group (e.g., thienyl, furyl, pyrrolyl, indolyl, 2-oxobenzothiazolyl-3-yl, imidazolidinyl, etc.).

The acylating reaction can be preferably carried out under a condition between a weak acidity and a weak alkalinity, namely, adjusting the fermentation broth to a suitable pH value with a base such as alkali metal hydroxide (e.g., sodium hydroxide, potassium hydroxide, etc.), alkali metal bicarbonate (e.g., sodium bicarbonate, potassium bicarbonate, etc.), alkali metal phosphate (e.g., sodium phosphate, potassium hydrogen phosphate, potassium hydrogen phosphate, etc.), alkali metal dihydrogen phosphate (e.g., sodium dihydrogen phosphate, potassium dihydrogen, etc.), tertiary organic base (e.g., trimethylamine, triethylamine, N-methylpiperazine, pyridine, etc.), and the like.

After the reaction is completed, the resulting acyl derivatives (II) of WS-3442 A,B,C,D and E can be isolated, and purified for example, by extracting the resultant reaction mixture with a solvent (e.g., ethyl acetate, methyl isobutyl ketone, etc.), removing the solvent from the extract, for example by evaporation, and then treating the resulting residue with a hydrophilic organic solvent (e.g., methanol, ethanol, acetone, tetrahydrofuran, dioxane, acetonitrile, etc.), after which the resultant may be treated, when desired, with a water immiscible organic solvent such as aromatic hydrocarbons (e.g., benzene, toluene, etc.), halo-substituted-aliphatic hydrocarbons, esters (e.g., ethyl acetate, etc.), or by conventional manners such as chromatography using silica gel, alumina, cellulose powder and the like. According to the procedure as mentioned above, the objective acyl derivatives may be easily isolated and purified in a free form or a salt form such as a metal salt (e.g., sodium salt, calcium salt, etc.), and an organic amine salt (e.g., dicyclohexylamine salt, trialkylamine salt, etc.).

The acyl derivatives (II) of these antibiotics WS-3442 A, B,C,D and E prepared by this invention which are all novel compounds, have activities against microorganisms and are useful as medicines, particularly, antibiotics.

The acyl derivative of antibiotic WS-3442 A, B, C, D and E of this invention is also useful for intermediate for preparing Cephalosporin derivatives having antimicrobiological activity. For example, the acyl derivative of WS-3442 A is deacylated, for example, hydrolyzed to give the compound of the formula:

, which is acylated to give the corresponding 7-acylated cephalosporin derivative, for example, CEX, i.e. 7-($\alpha$-aminophenylacetoamido)-3-methyl-3-cephem-4-carboxylic acid (ref: U.S. Pat. No. 3,507,861).

The following examples are given for the purpose of illustrating this invention.

EXAMPLE 1

The vegetative medium has the following ingredients:
Glycerin—3%
Soybean meal—2%
Gluten meal —1%
Cottonseed meal—1%
D.L-methionine—0.2%
Tap water—q.s.

100 ml. of the medium in each of thirty 500 ml. flasks was sterilized by a conventional method and then inoculated with spores and mycelia of *Streptomyces wadayamensis* ATCC 21948. These first seed cultures were incubated at 30° C. for 48 hours.

On the other hand, the culture medium (60 liters) above mentioned with an antifoaming agent (60 ml) in 200 literes tank fermentor was also sterilized by a conventional method. Whole volume of the first seed cultures were inoculated in this tank fermentor. This second seed culture was incubated at 30° C. for 24 hours.

Furthermore, the culture medium (650 liters) above mentioned with an antifoaming agent (300 ml) in 1 ton tank fermentor was sterilized by a conventional method. Whole volume of the second seed culture was incubated at 30° C. for 96 hours.

After the fermentation was completed, diaton earth was added to the culture broth with stirring. The culture broth was filtrated under increasing pressure by precoated filter press. The filtrate obtained (640 liters) was adjusted to pH 4–5 and to the filtrate was added activated carbon (20 kg). The carbon cake obtained by filtration was extracted with 80% aqueous acetone (600 liters). The acetone extract was concentrated and adjusted to pH 3.0 with the cation exchange resin Deolite C-20 (H+—form) (trade mark) and then passed through a column packed with an anion exchange resin Deolite A-6 (CH$_3$COO$^-$ form) (trade mark). Active material was eluted with 150 l of a pyridine-acetic acid-water mixture (100:7:900). The eluate was concentrated to a volume of about 8 l. and adjusted to pH 3.0 with Deolite C-20 (H+ form) (trade mark). From the concentrated solution, impurities were removed by washing twice with ethyl acetate and once with n-butanol. The aqueous layer obtained was passed through a column of Amberlite XAD-2 (trade mark) and then the passed solution was passed through a column of AF resin (CH$_3$COO$^-$ form) (trade mark). After the column was washed with water, active material was eluted with about 10 l. of a pyridine-acetic acid-water mixture (100:7:900). The eluate was concentrated and then adjusted to pH 3.0 with Deolite C-20 (H+ form) (trade mark). Impurities were removed by washing twice with ethyl acetate and once with n-butanol. The aqueous layer was adjusted to pH 5–6 with aqueous sodium hydroxide solution and then concentrated. To the concentrate was added a methanol-acetone mixture (1:3) in volume 5 times the concentrate's to give precipitate. The precipitate was collected and dried to yield crude powder (about 25 g).

The crude powder was chromatographed on a cellulose column with a n-butanol-acetic acid-water mixture (4:1:2). Eluate of active material was confirmed with thin layer chromatography (using cellulose sheet) by examining antibacterial activity, UV absorption, Nihydrin reaction and Rf value (0.46–0.48). Active fractions were collected. The eluate was concentrated, and acetone was added thereto to give precipitate. The precipitate was washed with acetone and then dissolved in water. The aqueous solution was adjusted to pH 6 with aqueous sodium hydroxide solution and lyophillized after desalting to give 18 g of WS-3442A as white powder.

EXAMPLE 2

A main fermentation broth obtained by fermenting in a similar manner to that as described in Example 1 was filtered. To the filtrate (8 l) was added acetone (1 l). The solution was adjusted to pH 7.5 with 10% aqueous sodium hydroxide solution while stirring at room temperature, and phenyl isocyanate (95 g) in acetone (150 ml) was added dropwise to the solution. The solution was adjusted to pH 7.5–8.0 with 10% aqueous sodium hydroxide solution. After stabilization of pH of the solution and confirming Ninhydrin reaction to be negative, diphenylurea was removed by filtration. Active material was extracted with ethyl acetate after the aqueous layer was adjusted to pH 1.0–1.5 with hydrochloric acid. The emulsion was filtered off. Active material in ethyl acetate layer was transferred into 3% sodium acetate solution. After the transferred solution was adjusted to pH 1.0–1.5 with 6 N hydrochloric acid, the active material was extracted with ethyl acetate. The extract was washed with a saturated sodium chloride aqueous solution and dried over magnesium sulfate. The solvent was distilled off under reduced pressure to give yellowish oily substance (28 g).

The oily substance was chromatographed using a silicagel column and developed with a ethyl acetate-acetic acid mixture (4:1) to give 5 g of 7-[5-(3-phenylureido)-5-carboxyvaleramido]-3-methyl-3-cephem-4-carboxylic acid as white powder.

| The nuclear magnetic resonance spectrum: | |
|---|---|
| δ (ppm) | |
| 1.80 | (4H, multiplet) |
| 1.90 | (3H, singlet) |
| 2.40 | (2H, multiplet) |
| 3.02–3.52 | (2H, quartet, J = 18HZ) |
| 4.17 | (1H, multiplet) |
| 5.06 | (1H, doublet, J = 4.5 HZ) |
| 5.55 | (1H, doublet, J = 4.5HZ) |
| 7.35 | (5H, multiplet) |

EXAMPLE 3

7-(5-t-butoxycarbonylamino-5-carboxyvaleramido)-3-methyl-3-cephem-4-carboxylic acid was given by substantially the same procedures as described in the Example 2 using t-butoxycarbonylazide as an acylating agent.

| The nuclear magnetic resonance spectrum: | |
|---|---|
| δ (ppm) | |
| 1.45 | (9H, singlet) |
| 1.70 | (4H, multiplet) |
| 1.95 | (3H, singlet) |
| 2.35 | (2H, multiplet) |
| 3.20–3.65 | (2H, quartet, J = 18HZ) |
| 3.90 | (1H, multiplet) |
| 5.08 | (1H, doublet J = 4.5HZ) |
| 5.55 | (1H, doublet, J = 4.5HZ) |

Thin layer chromatography:
Solvent system: acetic acid - ethyl acetate (1:2)
Rf = 0.68

EXAMPLE 4

The vegetative medium has following ingredients:
Glycerin—3%
Soybean meal—2%
Gluten meal—1%
Cotton seed meal—1%
D.L-methionine—0.2%
Tap water—q.s.

100 ml. of the medium in each of thirty 500 ml. flasks was sterilized by a conventional method and then inoculated with spores and mycelia of *Streptomyces wadayamensis* ATCC 21948. These first seed cultures were incubated at 30° C. for 48 hours.

On the other hand, the culture medium (60 liters) above mentioned with an antifoaming agent (60 ml) in 200 liters tank fermentor was sterilized by a conventional method. Whole volume of the first seed cultures were inoculated in this tank fermentor. This second seed culture was incubated at 30° C. for 24 hours.

Furthermore, the culture medium (650 liters) above mentioned with an antifoaming agent (300 ml) in 1 ton tank fermentor was sterilized by conventional method. Whole volume of the second seed culture was inoculated in this 1 ton tank fermentor. The main culture was incubated at 30° C. for 96 hours.

After the fermentation, diaton earth was added to the culture broth with stirring. The culture broth was filtered under increasing pressure by precoated filter press to give filtrate (640 l.). To the filtrate (8 l.) was added acetone (1 l.) and the solution was stirred. The solution was adjusted to pH 7.5 with 10% aqueous sodium hydroxide solution while stirring at room temperature and phenyl isocyanate (95 g) in acetone (150 ml.) was added dropwise to the solution.

The solution was adjusted to pH 7.5–8.0 with 10% aqueous sodium hydroxide solution. After stabilization of pH of the solution and confirming Ninhydrin reaction to be negative, diphenylurea was removed by filtration. Active material was extracted with ethyl acetate after the aqueous layer was adjusted to pH 1.0–1.5 with hydrochloric acid. The emulsion was filtered off and active material in ethyl acetate layer was transferred into 3% sodium acetate solution. After the transfered solution was adjusted to pH 1.0–1.5 with 6 N hydrochloric acid the active material was extracted with ethyl acetate. The extract was washed with saturated sodium chloride aqueous solution and dried over magnesium sulfate. By removing the solvent under reduced pressure, yellowish oily substance (28 g) was obtained.

The oily substance was chromatographed on a silicagel column, and developed with a ethyl acetate-acetic acid mixture (4:1) to give 5 g. of 7-[5-(3-phenylureido)-5-carboxyvaleramido]-3-methyl-3-cephem-4-carboxylic acid as white powder.

| The nuclear magnetic resonance spectrum: | |
|---|---|
| δ (ppm) | |
| 1.80 | (4H, multiplet) |
| 1.90 | (3H, singlet) |
| 2.40 | (2H, multiplet) |
| 3.02–3.52 | (2H, quartet, J = 18HZ) |
| 4.17 | (1H, multiplet) |
| 5.06 | (1H, doublet J = 4.5HZ) |
| 5.55 | (1H, doublet J = 4.5HZ) |
| 7.35 | (5H, multiplet) |

EXAMPLE 5

The vegetative medium has following ingredients:
Glycerin—3%
Soybean meal—2%
Gluten meal—1%
Cottonseed meal—1%
D.L-methiohine—0.2%
Tap water—q.s.

100 ml. of the medium in each of thirty 500 ml. flasks was sterilized by a conventional method and then inoculated with spores and mycelia of *Streptomyces wadayamensis* ATCC 21948. These first seed cultures were incubated at 30° C. for 48 hours.

On the other hand, the culture medium (60 liters) above mentioned with an antifoaming agent (60 ml) in 200 literes tank fermentor was sterilized by a conventional method. Whole volume of the first seed cultures were inoculated in this tank fermentor. This second seed culture was incubated at 30° C. for 24 hours.

Furthermore, the culture medium (650 liters) above mentioned with an antifoaming agent (300 ml) in 1 ton tank fermentor was sterilized by a conventional method. Whole volume of the second seed culture was incubated at 30° C. for 96 hours.

After the fermentation was completed, diaton earth was added to the culture broth with stirring. The culture broth was filtrated under increasing pressure by precoated filter press. The filtrate obtained (640 liters) was adjusted to pH 4–5 and to the filtrate was added activated carbon (20 kg). The carbon cake obtained by filtration was extracted with 80% aqueous acetone (600 liters). The acetone extract was concentrated and adjusted to pH 3.0 with cation exchange resin Deolite C-20 (H+-form) (trade mark) and then passed through a column of the anion exchange resin Deolite A-6 (CH3COO− form) (trade mark). The active material was eluted with 150 l of a pyridineacetic acid-water mixture (100:7:900). The eluate was concentrated to a volume of about 8 l. and adjusted to pH 3.0 with Deolite C-20 (H+ form) (trade mark). From the concentrated solution, impurities were removed by washing twice with ethyl acetate and once with n-butanol. The aqueous layer obtained was passed through a column of Amberlite XAD-2 (trade mark) and then the passed solution was passed through a column of AF resin (CH3COO− form) (trade mark). After the column was washed with water, active material was eluted with about 10 l. of a pyridine-acetic acid-water mixture (100:7:900). The eluate was concentrated and then adjusted to pH 3.0 with Deolite C-20 (H+ form) (trade mark). Impurities were removed by washing twice with ethyl acetate and once with n-butanol. The aqueous layer was adjusted to pH 5–6 with aqueous sodium hydroxide solution and then concentrated. To the concentrate was added a methanol-acetone mixture (1:3) in volume 5 times the concentrate's to give precipitate. The precipitate was collected and dried to yield crude powder (about 25 g).

The crude powder was chromatographed on a column of cellulose. Active material was eluted with a n-butanol-acetic acid-water mixture (4:1:2). The Eluate of active material was confirmed with thin layer chromatography (using cellulose sheet) by examining antibacterial activity, UV absorption, ninhydrin reaction and Rf value (0.27–0.30). Active fractions were collected. The eluate was concentrated and acetone was added to the concentrated solution to form precipitates. The precipitates were dried and chromatographed on a column of cellulose. The active material was eluted with a acetonitrile-propanol-water mixture (2:2:1).

The fractions exhibiting a marked antibacterial activity against *Escherichia coli* and giving Rf value (ca. 0.3) were collected. Further, the fractions exhibiting a marked antibacterial activity against *Bacillus subtilis* and giving Rf value (ca. 0.3) were collected. Each solution of the two kinds of the fractions obtained above was concentrated and to each resulting concentrate was added acetone to give precipitate respectively. Each precipitate was lyophillized to give 50 g of WS-3442 C from the former fraction (exhibiting antibacterial activity against *Esherichia coli*) and to give 50 g of WS-3442 B from the latter (exhibiting antibacterial activity against *Bacillus subtilis*).

EXAMPLE 6

A main fermentation broth obtained by fermenting in a similar manner to that as described in Example 5 was filtered.

The filtrate (0.8 l) was adjusted to pH 7.5 with 1N aqueous sodium hydroxide solution under cooling, and acetone (700 ml) was added to the filtrate. Phenyl isocyanate (35 ml) in acetone (35 ml) was added dropwise to the solution and the solution was adjusted to pH 7.5–8.0 with 1N aqueous sodium hydroxide solution. After stabilization of pH of the solution and confirming Ninhydrin reaction to be negative, diphenylurea was removed by filtration. The active material was extracted with ethyl acetate after the aqueous layer was adjusted to pH 1.0–1.5 with hydrochloric acid. The emulsion was filtered off. The active material in ethyl acetate layer was transferred into 3% sodium acetate solution. After the transfered solution was adjusted to pH 1.0–1.5 with 6 N hydrochloric acid, the active material was extracted with ethyl acetate. The extract was washed with saturated sodium chloride aqueous solution and dried over magnesium sulfate.

The solvent was distilled off under reduced pressure to give yellowish oily substance (29.7 g).

The oily substance was dissolved in methanol (100 ml) and to the solution was added dicyclohexylamine (18.5 g) under cooling. To the solution was added ether (250 ml) and the solution was allowed to stand to give crystals. The crystals were suspended in ethyl acetate and the suspension was treated with 1N hydrochloric acid to give 1.2 g of 7-[5-(3-phenylureido)-5-carboxyvaleramido]-3-(carbomoyloxymethyl)-3-cephem-4-carboxylic acid.

| The nuclear magnetic resonance spectrum: |
|---|
| Solvent: deuterium + sodium bicarbonate |

-continued

| δ (ppm) | Internal standard: TMS |
| --- | --- |
| 1.80 | (4H, multiplet) |
| 2.40 | (2H, multiplet) |
| 3.08–3.55 | (2H, quartet, J = 18HZ) |
| 4.15 | (1H, multiplet) |
| 5.05 | (1H, doublet, J = 4.5HZ) |
| 5.60 | (1H, doublet, J = 4.5HZ) |
| 7.35 | (5H, multiplet) |

Thin layer chromatography:

Solvent system: acetic acid-ethyl acetate (1:2)
Rf = 0.39

EXAMPLE 7

A main fermentation broth obtained by fermenting in a similar manner to that as described in Example 5 was filtered.

The filtrate (8 l) was adjusted to pH 7.5 with 1N aqueous sodium hydroxide solution under cooling and acetone (1 l) was added to the filtrate. Phenyl isocyanate (95 g) in acetone (150 ml) was added dropwise to the solution and the solution was adjusted to pH 7.5–8.0 with 10% aqueous sodium hydroxide solution. After stabilization of pH of the solution and confirming Ninhydrin reaction to be negative, diphenylurea was removed by filtration. The active material was extracted with ethyl acetate after the aqueous layer was adjusted to pH 1.0–1.5 with hydrochloric acid. The emulsion was filtered off. The active material in ethyl acetate layer was transfered into 3% sodium acetate solution. After the transfered solution was adjusted to pH 1.0–1.5 with 6 N hydrochloric acid, the active material was extracted with ethyl acetate. The extract was washed with saturated sodium chloride aqueous solution and dried over magnesium sulfate.

The solvent was distilled off under reduced pressure to give yellowish oily substance (28 g).

The oily substance was chromatographed on a column of silicagel and developed with ethyl acetate-acetic acid mixture (4:1) to give 10 g of 7-[5-(3-phenylureido)-5-carboxyvaleramido]-3-(carbamoyloxymethyl)-7-methoxy-3-cephem-4-carboxylic acid as white powder.

| δ (ppm) | The nuclear magnetic resonance: |
| --- | --- |
| | Solvent: deuterium + sodium bicarbonate |
| | Internal standard + TMS |
| 1.80 | (4H, multiplet) |
| 2.40 | (2H, multiplet) |
| 3.02–3.53 | (2H, quartet, J = 18HZ) |
| 3.54 | (3H, singlet) |
| 4.18 | (1H, multiplet) |
| 5.15 | (1H, singlet) |
| 7.30 | (5H, multiplet) |

Thin layer chromatography:

Solvent system: acetic acid-ethyl acetate (1:2)
Rf = 0.39

EXAMPLE 8

7-(5-t-butoxycarbonylamino-5-carboxyvaleramido)-3-(carbamoyloxymethyl)-7-methoxy-3-cephem-4-carboxylic acid was given by substantially the same procedures as described in the Example 7 using t-butoxycarbonylazide as acylating agent.

| δ (ppm) | The nuclear resonance spectrum: |
| --- | --- |
| | Solvent: deuterium + sodium bicarbonate |
| | Internal standard: TMS |
| 1.43 | (9H, singlet) |
| 1.75 | (4H, multiplet) |
| 2.40 | (2H, multiplet) |
| 3.25–3.72 | (2H, quartet, J = 18HZ) |
| 3.53 | (3H, singlet) |
| 3.85 | (1H, multiplet) |
| 5.16 | (1H, singlet) |

Thin layer chromatography:

Solvent: acetic acid:ethyl acetate (1:2)
Rf = 0.49

EXAMPLE 9

The vegetative medium has following ingredients:
Glycerin—3%
Soybean meal—2%
Gluten meal—1%
Cottonseed meal—1%
D.L-methionine—0.2%
Tap water—q.s.

100 ml. of the medium in each of thirty 500 ml. flasks was sterilized by a conventional method and then inoculated with spores and mycelia of *Streptomyces wadayamensis* ATCC 21948.

These first seed cultures were incubated at 30° C. for 48 hours.

On the other hand, the culture medium (60 l.) above mentioned with an antifoaming agent (60 ml) in 200 l. tank fermentor was sterilized by a conventional method. Whole volume of the first seed cultures were inoculated in this tank fermentor. This second seed culture was incubated at 30° C. for 24 hours.

Furthermore, the culture medium (650 l.) above mentioned with an antifoaming agent (300 ml) in 1 ton tank fermentor was sterilized by a conventional method. Whole volume of the second seed culture was incubated at 30° C. for 96 hours.

After the fermentation was completed, diaton earth was added to the culture broth with stirring. The culture broth was filtrated under increasing pressure by precoated filter press to give filtrate (640 l.).

The filtrate (0.8 l) was adjusted to pH 7.5 with 1N aqueous sodium hydroxide solution under cooling and acetone (700 ml) was added to the filtrate. Phenyl isocyanate (35 ml) in acetone (3.5 ml) was added dropwise to the solution and the solution was adjusted to pH 7.5–8.0 with 1N aqueous sodium hydroxide solution. After stabilization of pH of the solution and confirming Ninhydrin reaction to be negative. Diphenylurea was removed by filtration. The active material was extracted with ethyl acetate after the aqueous layer was adjusted to pH 1.0–1.5 with hydrochloric acid. The emulsion was filtered off. The active material in ethyl acetate layer was transferred into 3% sodium acetate solution. After the transferred solution was adjusted to pH 1.0–1.5 with 6 N hydrochloric acid, the active material was extracted with ethyl acetate. The extract was washed with a saturated sodium chloride aqueous solution and dried over magnesium sulfate. The solvent was distilled off under reduced pressure to give yellowish oily substance (29.7 g).

The oily substance was dissolved in methanol (100 ml) and to the solution was added dicyclohexylamine (18.5 g) under cooling. To the solution was added ether (250 ml) and the solution was allowed to stand to give crystals. The crystals were suspended in ethyl acetate and the suspension was treated with 1N hydrochloric acid to give 1.2 g of 7-[5-(3-phenylureido)-5-carboxyvaleramido]-3-(carbamoyloxymethyl)-3-cephem-4-carboxylic acid.

The nuclear magnetic resonance spectrum:
Solvent: deuterium + sodium bicarbonate
Internal standard: TMS

| δ (ppm) | |
| --- | --- |
| 1.80 | (4H, multiplet) |
| 2.40 | (2H, multiplet) |
| 3.08–3.55 | (2H, quartet, J = 18HZ) |
| 4.15 | (1H, multiplet) |
| 5.05 | (1H, doublet, J = 4.5HZ) |
| 5.60 | (1H, doublet, J = 4.5HZ) |
| 7.35 | (5H, multiplet) |

Thin layer chromatoraphy:
Solvent system: acetic acid-ethyl acetate (1:2)
Rf = 0.39

EXAMPLE 10

The vegetative medium has following ingredients:
Glycerin—3%
Soybean meal—2%
Gluten meal—1%
Cottonseed meal—1%
D.L-methionine—0.2%
Tap water—q.s.

100 ml. of the medium in each of thirty 500 ml. flasks was sterilized by a conventional method and then inoculated with spores and mycelia of Streptomyces wadayamensis ATCC 21948. These first seed cultures were incubated at 30° C. for 48 hours.

On the other hand, the culture medium (60 liters) above mentioned with an antifoaming agent (60 ml) in 200 literes tank fermentor was sterilized by a conventional method. Whole volume of the first seed cultures were inoculated in this tank fermentor. This second seed culture was incubated at 30° C. for 24 hours.

Furthermore, the culture medium (650 liters) above mentioned with an antifoaming agent (300 ml) in 1 ton tank fermentor was sterilized by a conventional method. Whole volume of the second seed culture was incubated at 30° C. for 96 hours.

After the fermentation was completed, diaton earth was added to the culture broth with stirring. The culture broth was filtrated under increasing pressure by precoated filter press to give filtrate (640 l.). The filtrate (8 l) was adjusted to pH 7.5 with 10% aqueous sodium hydroxide solution under cooling and acetone (1 l) was added to the filtrate. Phenyl isocyanate (95 g) in acetone (150 ml) was added dropwise to the solution and the solution was adjusted to pH 7.5–8.0 with 10% aqueous sodium hydroxide solution. After stabilization of pH of the solution and confirming Ninhydrin reaction to be negative, diphenylurea was removed by filtration. The active material was extracted with ethyl acetate after the aqueous layer was adjusted to pH 1.0–1.5 with hydrochloric acid. The emulsion was filtered off. The active material in ethyl acetate layer was transferred into 3% sodium acetate solution. After the transferred solution was adjusted to pH 1.0–1.5 with 6 N hydrochloric acid, the active material was extracted with ethyl acetate. The extract was washed with a saturated sodium chloride aqueous solution and dried over magnesium sulfate. The solvent was distilled off under reduced pressure to give yellowish oily substance (28 g).

The oily substance was chromatographed on a column of silicagel and developed in ethyl acetate—acetic acid mixture (4:1) to give 10 g of 7-[5-(3-phenylureido)-5-carboxyvaleramido]-3-(carbamoyloxymethyl)-7-methoxy-3-cephem-4-carboxylic acid as white powder.

The nuclear magnetic resonance:
Solvent: deuterium + sodium bicarbonate
Internal standard: TMS

| δ (ppm) | |
| --- | --- |
| 1.80 | (4H, multiplet) |
| 2.40 | (2H, multiplet) |
| 3.02–3.53 | (2H, quartet, J = 18HZ) |
| 3.54 | (3H, singlet) |
| 4.18 | (1H, multiplet) |
| 5.15 | (1H, singlet) |
| 7.30 | (5H, multiplet) |

Thin layer chromatography:
Solvent system: acetic acid-ethyl acetate (1:2)
Rf = 0.39

EXAMPLE 11

The vegetative medium has following ingredients:
Glycerin—3%
Soybean meal—2%
Gluten meal—1%
Cottonseed meal—1%
D.L-methionine—0.2%
Tap water—q.s.

100 ml. of the medium in each of thirty 500 ml. flasks was sterilized by a conventional method and then inoculated with spores and mycelia of *Streptomyces wadayamensis* ATCC 21948. These first seed cultures were incubated at 30° C. for 48 hours.

On the other hand, the culture medium (60 liters) above mentioned with an antifoaming agent (60 ml) in 200 literes tank fermentor was sterilized by a conventional method. Whole volume of the first seed cultures were inoculated in this tank fermentor.

This second seed culture was incubated at 30° C. for 24 hours.

Furthermore, the culture medium (650 liters) above mentioned with an antifoaming agent (300 ml) in 1 ton tank fermentor was sterilized by a conventional method. Whole volume of the second seed culture was incubated at 30° C. for 96 hours.

After the fermentation was completed, diaton earth was added to the culture broth with stirring. The culture broth was filtrated under increasing pressure by precoated filter press. The filtrate obtained (640 liters) was adjusted to pH 4–5 and to the filtrate was added activated carbon (20 kg). The carbon cake obtained by filtration was extracted with 80% aqueous acetone (600 l.). The acetone extract was concentrated and adjusted to pH 3.0 with a cation exchange resin Deolite C-20 ($H^+$-form) (trade mark) and then passed through a column of an anion exchange resin Deolite A-6 ($CH_3COO^-$ form) (trade mark). Active material was eluted with 150 l of a pyridineacetic acid-water-mixture (100:7:900). The eluate was concentrated to a volume of about 8 l. and adjusted to pH 3.0 with Deolite C-20 (H+ form) (trade mark). From the concentrated solution, impurities were removed by washing twice with ethyl acetate and once with n-butanol. The aqueous layer obtained was passed through a column of Amberlite XAD-2 (trade mark) and then the passed solution was passed through a column of AF resin (CH₃COO⁻ form) (trade mark). After the column was washed with water, active material was eluted with about 10 l. of a pyridine-acetic acid-water mixture (100:7:900). The eluate was concentrated and then adjusted to pH 3.0 with Deolite C-20 (H+ form) (trade mark). Impurities were removed by washing twice with ethyl acetate and once with n-butanol. The aqueous layer was adjusted to pH 5-6 with aqueous sodium hydroxide solution and then concentrated. To the concentrate was added a methanol-acetone mixture (1:3) in volume five times the concentrate's to give precipitate. The precipitate was collected and dried to yield crude powder (about 25 g).

The crude powder was chromatographed on a column of cellulose. Active material was eluted with a n-butanol-acetic acid-water mixture (4:1:2). Eluate of active material was confirmed with thin layer chromatography (using cellulose sheet) by examining antibacterial activity, UV absorption, Nihydrin reaction and Rf value (0.48-0.50). Active fractions were collected. The eluate was concentrated, and acetone was added thereto to give precipitates. The precipitate was washed with acetone and then dissolved in water. The aqueous solution was adjusted to pH 6 with aqueous sodium hydroxide solution and lyophillized after desalting to give 4 g of WS-3442 D as white powder.

EXAMPLE 12

A main fermentation broth obtained by fermenting in a similar manner to that as described in Example 11 was filtered. To the filtrate (1.0 l) was added acetone (200 ml) and phenylisocyanate (15 ml) in acetone (15 ml) was added dropwise to the solution while stirring at room temperature. The solution was adjusted to pH 7.5-8.0 with 1N aqueous sodium hydroxide solution. After stabilization of pH of the solution and confirming Ninhydrin reaction to be negative, diphenylurea was removed by filtration. The active material was extracted with ethyl acetate after the aqueous layer was adjusted to pH 1.0-1.5 with hydrochloric acid. The emulsion was filtered off. The active material in ethyl acetate layer was transferred into 3% sodium acetate solution. After the transferred solution was adjusted to pH 1.0-1.5 with 6 N hydrochloric acid, active material was extracted with ethyl acetate. The extract was washed with a saturated sodium chloride aqueous solution and dried over magnesium sulfate. The solvent was distilled under reduced pressure to give yellowish oily substance (4 g).

The oily substance was columnchromatographed using silicagel. The column was developed in an ethyl acetate-acetic acid mixture (4:1) to give 50 mg of 7-[5-(3-phenylureido)-5-carboxyvaleramido]-3-methyl-7-methyoxy-3-cephem-4-carboxylic acid

| The nuclear magnetic resonance spectrum: | |
|---|---|
| Solvent: deuterium + sodium bicarbonate Internal standard: TMS | |
| δ (ppm) | |
| 1.80 | (4H, multiplet) |
| 1.88 | (3H, singlet) |
| 2.45 | (2H, multiplet) |
| 2.93-3.44 | (2H, doublet, J = 18HZ) |
| 3.54 | (3H, singlet) |
| 4.18 | (1H, multiplet) |
| 5.08 | (1H, singlet) |
| 7.35 | (5H, multiplet) |

Thin layer chromatography:
Solvent system: acetic acid-ethyl acetate (1:2)
Rf = 0.56

EXAMPLE 13

7-(5-t-butoxycarbonylamino-5-carboxyvaleramido)-3-methyl-7-methoxy-3-cephem-4-carboxylic acid was given by substantially the same procedures as described in the Example 12 using t-butoxycarbonylazide as acylating agent.

| The nuclear magnetic resonance spectrum: | |
|---|---|
| Solvent: deuterium + sodium bicarbonate Internal standard: TMS | |
| δ (ppm) | |
| 1.43 | (9H, singlet) |
| 1.75 | (4H, multiplet) |
| 1.92 | (3H, singlet) |
| 2.40 | (2H, multiplet) |
| 3.10-3.60 | (2H, doublet, J = 18HZ) |
| 3.51 | (3H, singlet) |
| 3.90 | (1H, multiplet) |
| 5.11 | (1H, singlet) |

Thin layer chromatography:
Solvent system: acetic acid-ethyl acetate (1:2)
Rf = 0.67

EXAMPLE 14

The vegetative medium has following ingredients:
Glycerin—3%
Soybean meal—2%
Gluten meal—1%
Cottonseed meal—1%
D.L—methionine—0.2%
Tap water—q.s.

100 ml. of the-medium in each of thirty 500 ml. flasks was sterilized by a conventional method and then inoculated with spores and mycelia of *Streptomyces wadayamensis* ATCC 21948. These first seed cultures were incubated at 30° C. for 48 hours.

On the other hand, the culture medium (60 liters) above mentioned with an antifoaming agent (60 ml) in 200 literes tank fermentor was also sterilized by a conventional method. Whole volume of the first seed cultures were inoculated in this tank fermentor. This second seed culture was incubated at 30° C. for 24 hours.

Furthermore, the culture medium (650 liters) above mentioned with an antifoaming agent (300 ml) in 1 ton tank fermentor was sterilized by a conventional method. Whole volume of the second seed culture was incubated at 30° C. for 96 hours.

After the fermentation was completed, diaton earth was added to the culture broth with stirring. The culture broth was filtrated under increasing pressure by precoated filter press to give filtrate (640 l.). To the filtrate (1.0 l) was added acetone (200 ml) and phenylisocyanate (15 ml) in acetone (15 ml) was added dropwise to the solution while stirring at room temperature. The solution was adjusted to pH 7.5-8.0 with 1N aqueous sodium hydroxide solution. After stabilization of pH of the solution and confirming Ninhydrin reaction to be negative, diphenylurea was removed by filtration. The active material was extracted with ethyl acetate after the aqueous layer was adjusted to pH 1.0-1.5 with hydrochloric acid. The emulsion was filtered off. The active material in ethyl acetate layer was transfered into 3% sodium acetate solution. After the transferred solution was adjusted to pH 1.0-1.5 with 6 N hydrochloric acid, the active material was extracted with ethyl acetate. The extract was washed with saturated sodium chloride aqueous solution and dried over magnesium sulfate. The solvent was distilled under reduced pressure to give yellowish oily substance (4 g).

The oily substance was chromatographed on a column of silicagel. The column was developed in ethyl acetate—acetic acid mixture (4:1) to give 50 mg of 7-[5-(3-phenylureido)-5-carboxyvaleramido]-3-methyl-7-methoxy-3-cephem-4-carboxylic acid.

The nuclear magnetic resonance spectrum:
Solvent: deuterium + sodium bicarbonate
Internal standard: TMS

| $\delta$ (ppm) | |
|---|---|
| 1.80 | (4H, multiplet) |
| 1.88 | (3H, singlet) |
| 2.45 | (2H, multiplet) |
| 2.93-3.44 | (2H, doublet, J = 18HZ) |
| 3.54 | (3H, singlet) |
| 4.18 | (1H, multiplet) |
| 5.08 | (1H, singlet) |
| 7.35 | (5H, multiplet) |

Thin layer chromatography:
Solvent system: acetic acid-ethyl acetate (1:2)
Rf = 0.56

EXAMPLE 15

The vegetative medium has following ingredients:
Starch—4%
Cottonseed meal—2%
Gluten meal—2%
Ebios (trademark)—1%
$KH_2PO_4$—0.1%
D.L-methionine—0.1%
Soybean oil—0.5%
Tap water—q.s.

100 ml. of the medium in each of thirty 500 ml. flasks was sterilized by a conventional method and then inoculated with spores and mycelia of Streptomyces wadayamensis ATCC 21948. These first seed cultures were incubated at 30° C. for 48 hours.

On the other hand, culture medium (60 l.) above mentioned with an antifoaming agent (60 ml) in 200 l. tank fermentor was sterilized by a conventional method. Whole volume of the first seed cultures were inoculated in this tank fermentor. This second seed culture was incubated at 30° C. for 24 hours.

Furthermore, main culture medium (650 l.) above mentioned with an antifoaming agent (300 ml) in 1 ton tank fermentor was sterilized by a conventional method. Whole volume of the second seed culture was inoculated in this 1 ton tank fermentor. The main culture was incubated at 30° C. for 96 hours.

After the fermentation was completed, diaton earth was added to these cultures with stirring. The culture broth was filtered under increasing pressure by precoated filter press. The culture filtrate (640 l.) obtained was heated at 100° C. for 20-30 minutes and then the filtrate was adjusted to pH 4. The filtrate was adjusted to pH 2-2.5 with cation exchange resin Deolite C-20 (H+ form) (trade mark) and charged on a column of AF resin ($CH_3COO^-$ form) (trade mark). After the column was washed with water, active material was eluted with a pyridine-acetic acid-water mixture (10:1:90). The eluate was concentrated. N-butanol was added to the concentrate and stirred.

The aqueous layer was diluted with water to 60 l. and the solution was passed through a column of Deolite A-6 ($CH_3COO^-$ form). The passed solution was concentrated and the concentrate was adjusted to pH 5-6 and then concentrated. Five volumes of methanol-acetone mixture (1:3) was added to the concentrate to form precipitate. The precipitate was collected and dried to yield crude powder (about 300 g).

This crude powder was chromatographed on a column of cellulose. The column was eluted with a acetonitrile-propanol-water mixture (2:2:1). Eluate was confirmed with thin layer chromatography (using cellulose sheet) by examining anti-bacterial activity, UV absorption, Ninhydrin reaction and Rf value (0.27). Active fractions were collected and concentrated. N-butanol was added to the concentrated solution and stirred.

The aqueous layer separated was diluted with water to 60 l. and the solution was passed through a column of an anion exchange resin Deolite A-6 ($CH_3COO^-$ form) (trade mark).

The passed solution was concentrated and the concentrate was adjusted to pH 5-7. A methanol-acetone mixture (1:1) was added to the concentrated solution to form precipitates. The precipitates was collected and dried to yield powder (150 g). This powder was chromatographed on a column of cellulose and developed with a acetonitrile-propanol-water mixture (2:2:1). The eluate was confirmed with thin layer chromatography (using cellulose sheet), by examining antibacterial activity, UV absorption, Ninhydrin reaction and Rf value (0.27). Active fractions were collected. Acetone was added to the fractions to give precipitate. The precipitate was washed with acetone and dissolved in water. The aqueous solution was adjusted to pH 6.0 with 1N aqueous sodium hydroxide solution and desalted and lyophillized to yield WS-3442 E (60 g).

EXAMPLE 16

7-[5-(3-phenylureido)-5-carboxyvaleramido]-3-hydroxymethyl-3-cephem-4-carboxylic acid is obtained according to a similar manner of Example 12.

The nuclear magnetic resonanse spectrum:
Solvent: deuterium + sodium bicarbonate
Internal standard: TMS

| $\delta$ (ppm) | |
|---|---|
| 1.80 | (4H, multiplet) |
| 2.42 | (2H, multiplet) |
| 3.62-3.65 | (2H, a.b quartet, J = 18HZ) |
| 4.20 | (1H, multiplet) |
| 4.26 | (2H, singlet) |
| 5.08 | (1H, doublet, J = 4.5HZ) |
| 5.63 | (1H, doublet, J = 4.5HZ) |
| 7.35 | (5H, multiplet) |

What we claim is:

1. A process for the production of antibiotic WS-3442 selected from the group of WS-3442 A, B, C, D and E in which

WS-3442 A has following chemical structure:

WS-3442 B has following chemical structure:

WS-3442 C has following chemical structure:

WS-3442 D has following chemical structure:

WS-3442 E has following chemical structure:

which comprises cultivating a WS-3442-producing strain of *Streptomyces wadayamensis* in an aqueous nutrient medium under submerged aerobic conditions until a substantial antibiotic activity is imparted to said medium by the production of the WS-3442 and recovering the WS-3442.

2. A process according to claim 1 which comprises cultivating a strain of *Streptomyces wadayamensis* ATCC 21948 in an aqueous nutrient medium under submerged aerobic conditions until substantial antibiotic activity is imparted to said medium by the production of the WS-3442 and recovering the WS-3442.

3. A process according to claim 1 which comprises cultivating *Streptomyces wadayamensis* in an aqueous nutrient medium containing a carbon source and nitrogen source.

4. A process according to claim 2 which comprises cultivating *Streptomyces wadayamensis* ATCC 21948 in an aqueous nutrient medium containing a carbon source and a nitrogen source.

5. A process according to claim 1, or 2, wherein WS-3442 A is recovered from the fermentation broth.

6. A process according to claim 1 or 2, wherein WS-3442 B is recovered from the fermentation broth.

7. A process according to claim 1 or 2, wherein WS-3442 C is recovered from the fermentation broth.

8. A process according to claim 1 or 2, wherein WS-3442 D is recovered from the fermentation broth.

9. A process according to claim 1 or 2, wherein WS-3442 E is recovered from the fermentation broth.

* * * * *